(12) United States Patent
Chapelle et al.

(10) Patent No.: US 11,478,165 B2
(45) Date of Patent: Oct. 25, 2022

(54) CARDIAC DEVICE

(71) Applicant: INRIA INSTITUT NATIONAL DE RECHERCHE EN INFORMATIQUE ET EN AUTOMATIQUE, Le Chesnay (FR)

(72) Inventors: Dominique Chapelle, Paris (FR); Sébastien Imperiale, Montrouge (FR); Alexandre Laurin, Paris (FR); Philippe Moireau, Paris (FR)

(73) Assignee: Inria Institut National De Recherche En Informatique Et En Automatique

( * ) Notice: Subject to any disclaimer, the term of this patent is extended or adjusted under 35 U.S.C. 154(b) by 780 days.

(21) Appl. No.: 16/081,752

(22) PCT Filed: Mar. 1, 2017

(86) PCT No.: PCT/FR2017/050468
§ 371 (c)(1),
(2) Date: Aug. 31, 2018

(87) PCT Pub. No.: WO2017/149250
PCT Pub. Date: Sep. 8, 2017

(65) Prior Publication Data
US 2021/0219870 A1    Jul. 22, 2021

(30) Foreign Application Priority Data
Mar. 2, 2016   (FR) ....................................... 1651760

(51) Int. Cl.
*A61B 5/11*    (2006.01)
*A61B 5/00*    (2006.01)

(52) U.S. Cl.
CPC .......... *A61B 5/1107* (2013.01); *A61B 5/7203* (2013.01); *A61B 5/725* (2013.01); *A61B 2562/0219* (2013.01)

(58) Field of Classification Search
None
See application file for complete search history.

(56) References Cited

U.S. PATENT DOCUMENTS

| 6,024,705 A | 2/2000 | Schlager et al. |
| 2011/0066041 A1 | 3/2011 | Pandia et al. |

FOREIGN PATENT DOCUMENTS

| WO | 2015107374 A1 | 7/2015 |
| WO | 2015120330 A1 | 8/2015 |

OTHER PUBLICATIONS

Caruel, et al., "Dimensional reductions of a cardiac model for effective validation and calibration," Biomechanics and Modeling in Mechanobiology, Dec. 8, 2013, pp. 897-914, vol. 13, No. 4, Berlin/Heidelberg.
Laurin, et al., "A 3D Model of the Thorax for Seismocardiography," Computing in Cardiology, 2015, pp. 465-468, vol. 42.

*Primary Examiner* — Ankit D Tejani
(74) *Attorney, Agent, or Firm* — Maynard Cooper & Gale, P. C.; Brian T. Sattizahn

(57) ABSTRACT

The invention relates to a cardiac device comprising an accelerometer (4) and a filter (6) arranged to eliminate noise from an SCG signal from the accelerometer (4), as well as a computer (8) arranged to apply a thoraco-cardiovascular model to the signal from the filter (6) and to obtain at least one cardiac activity indicator (CI) from same.

10 Claims, 2 Drawing Sheets

CARDIAC DEVICE

The invention relates to the field of cardiac monitoring.

It is known to perform ECGs (electrocardiograms) to perform medical monitoring of a patient having a cardiac condition. Some cardiac conditions require daily or even continuous monitoring. In this context, patients may live at home, but it is necessary for ECGs to be performed on them several times a day.

ECGs are examinations that are non-invasive but inconvenient due to the fact that they require several electrodes to be placed fairly accurately and the use of a specific apparatus. On a day-to-day basis, using these apparatuses poses numerous problems and significantly reduces patients' mobility, and the information derived from them remains incomplete as it reveals nothing with regard to the mechanical state of the system (pressures and outputs, etc.).

There are examinations called SCGs (seismocardiograms) that show the data on cardiac activity measured by an accelerometer. This examination is less inconvenient than the ECG, as it is performed by applying an accelerometer to the thorax of a patient and by taking account of the measurements acquired. In addition, the SCG contains information with regard to the mechanics of the cardiovascular system, unlike the ECG.

However, directly interpreting the information contained in an SCG, other than the heart rate itself, is highly difficult given the complexity of the underlying phenomena, and these measurements are de facto not used to a great extent at the present time.

The invention aims to improve the situation. To this end, the invention proposes a cardiac device comprising an accelerometer, and a filter arranged to remove noise from an SCG signal derived from the accelerometer, and furthermore comprises a computer arranged to apply a thoraco-cardiovascular model to the signal coming from the filter and to derive at least one cardiac activity indicator therefrom.

This device is particularly advantageous as it makes it possible to perform cardiac monitoring using widely available and inexpensive hardware, without invasive measurements, and is able to be performed outside of a clinical environment, giving access to important cardiac indicators with regard to cardiovascular mechanics, outside of the scope of an ECG.

According to diverse variants, the device may have one or more of the following features:
- the computer is arranged to compute a cardiac activity indicator by applying a thoraco-cardiovascular model in order to compute a theoretical SCG signal value, and by applying at least one correction function based on the difference between the theoretical SCG signal value and the value derived from the filter,
- the computer is arranged to apply at least one Kalman filter or a combination of a Kalman filter and a Luenberger observer in said at least one correction function,
- the thoraco-cardiovascular model comprises a cardiovascular model, a cardiothoracic force transfer function and a thoracic mechanical model,
- the accelerometer and the computer are accommodated in a single housing of the device,
- the accelerometer and the computer are accommodated in a two separate housings of the device,
- the device is arranged to transmit a signal as a function of a comparison between a computed cardiac activity indicator and a threshold value, and
- the computer is arranged to receive and process variables linked to hemodynamics.

The invention also relates to a cardiac monitoring method, comprising:
- obtaining an SCG signal from an accelerometer,
- filtering the SCG signal,
- applying a thoraco-cardiovascular model to the filtered SCG signal and taking at least one cardiac activity indicator therefrom.

According to this method, the application of the thoraco-cardiovascular model may comprise:
- applying a thoraco-cardiovascular model in order to compute a theoretical SCG signal value,
- determining a difference between the theoretical SCG signal value and the value of the filtered SCG signal,
- applying at least one correction function based on the difference in order to determine the cardiac activity indicator.

Other features and advantages of the invention will become more apparent upon reading the following description, taken from examples given by way of nonlimiting illustration, taken from the drawings, in which.

The drawings and the description hereinafter contain, above all, elements of a certain nature. They may therefore not only serve for improved understanding of the present invention, but also contribute to the definition thereof where appropriate.

The present description is such that it involves elements liable to be protected under trademark and/or copyright. The rights holder has no objection to anyone making identical reproductions of the present patent document or its description as it appears in official records. For the rest, the holder reserves its rights in their entirety.

Furthermore, the detailed description is supplemented by Appendix A, which gives the formulation of certain mathematical formulae used in the context of the invention. This Appendix is provided separately for the sake of clarity and to facilitate referrals. It forms an integral part of the description, and may therefore not only serve for improved understanding of the present invention, but also contribute to the definition thereof where appropriate.

Figure 1:
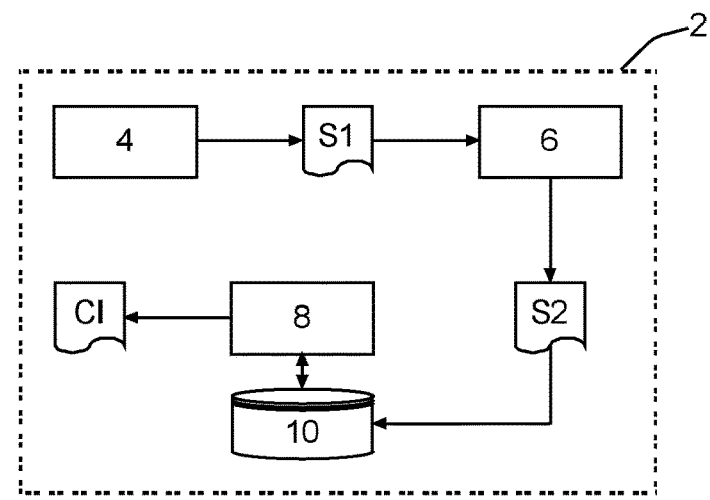
FIG. 1 shows a general diagram of a device according to the invention.

FIG. 1 shows a general diagram of a device 2 according to the invention. The device 2 comprises an accelerometer 4, a filter 6, a computer 8 and a memory 10.

In the example described here, the device 2 is a smartphone. Thus, the smartphone is positioned against the thorax of a patient, preferably directly in contact with the skin, but, as a variant, the patient may keep a T-shirt or a shirt on, with a sweater running the risk of damping the vibrations produced by the heartbeats to too great an extent. Thus, all of the elements of the device are contained in a single object that, by its nature, is kept close by the patient. As a variant, the elements of the device 2 could be separate, the accelerometer 4 being accommodated in a housing and kept in contact with the thorax of the patient and communicating in a wired or wireless manner with another housing enclosing the other elements.

In the context of the invention, the filter 6 and the computer 8 are elements that access the memory 10 directly or indirectly. They may be implemented in the form of an appropriate computer code executed on one or more processors. Processors should be understood to mean any suitable processor. Such a processor may be implemented in any known manner, in the form of a microprocessor for a personal computer, of a dedicated chip of FPGA or SoC (system on chip) type, of a computing resource on a grid, of a microcontroller, or any other form suitable for providing the computational power required for the implementation described below. One or more of these elements may also be implemented in the form of specialized electronic circuits, such as an ASIC. A combination of processor and electronic circuits may also be contemplated.

In the context of the invention, the memory 10 may be any type of data store able to receive digital data: hard drive, flash memory hard drive (SSD), flash memory in any form, random access memory, magnetic disk, locally distributed or cloud storage, etc. The data computed by the device may be stored on any type of memory similar to the memory 10 or on the latter. These data may be deleted after the device has performed its tasks, or kept.

Figure 4:
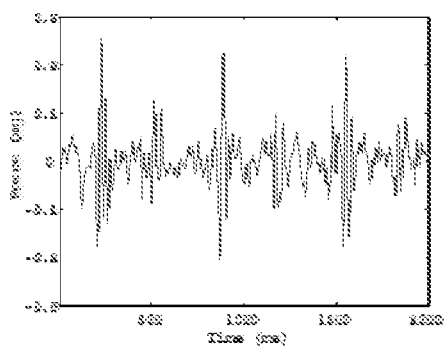

When the device is placed against the thorax of a patient and the acquisition of cardiac data is launched, the accelerometer 4 measures the vibrations of the thoracic cavity of the patient and produces a signal S1. FIG. 4 shows an example of a signal obtained at the output of the accelerometer 4.

The signal S1 is then processed by the filter 6, in particular in order to remove noise therefrom. Specifically, the signal coming from the accelerometer 4 (shown in FIG. 4) has a high noise component, in particular due to the fact that the accelerometer is not in perfect contact with the thorax and the patient is liable to move slightly during the measurement, etc.

Figure 5:
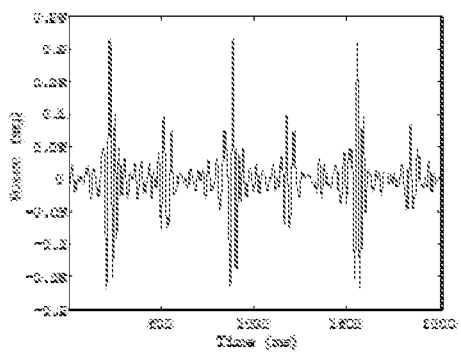

This noise removal is intended mainly to filter the signal, identify the sections including high noise, and interpolate data therein. The filter is a bandpass filter used to isolate the frequencies of interest, as shown in FIG. 5. The filtered signal is then compared with a reference signal in order to identify the zones where noise prevents analysis from the outset. The clean zones bounding the noisy zones are then used either to analyze the noisy zones or to replace them.

Figure 6:
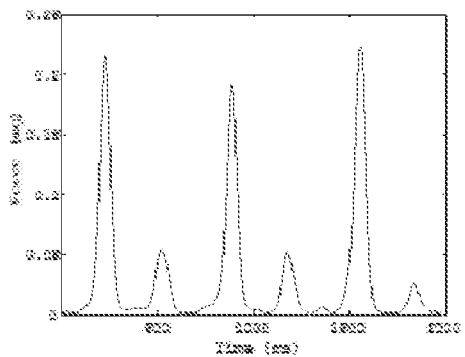

The filter 6 produces a signal S2, one example of which is shown in FIG. 6, which corresponds to the signal S1 with noise removed. Next, the computer 8 applies a thoraco-cardiovascular model to the signal S2 so as to derive cardiac information CI therefrom. In the example described here, the signal S1, the signal S2 and the data CI are stored in the memory 10 with the thoraco-cardiovascular model.

The thoraco-cardiovascular model comprises:
a cardiovascular model linking parameters for modeling the heart (modulus of elasticity, contractility, maximum active tension of the muscle fibers, etc.), variables representative of the state of the heart, in particular describing its deformations, and blood circulation (arterial elastance, peripheral resistance, arterial and venous pressure, etc.), a law representing the contact forces applied to the thoracic cavity by the heart, as a function of the cardiac parameters and optionally of parameters representing the position (vertical/horizontal, etc.) of the patient, and
a thoracic model comprising a transfer function between the contact forces applied by the heart and the acceleration induced in the thoracic cavity.

In the example described here, the monitored cardiac condition is typically chronic cardiac failure, for example of 'dilated cardiomyopathy' (DCM) type. In this case, the monitoring is intended to prevent risks of aggravation, in particular of acute decompensated heart failure, by adapting the patient's treatment as a function of the change in his state.

In the case described here, the cardiac variables that a cardiologist will want to monitor comprise the variation in the radius of the left ventricular cavity (hereinafter y), the deformation of the muscle fibers (hereinafter ec), the cardiac active stiffness (hereinafter kc), the cardiac active strain (hereinafter tc), the aortic pressure (hereinafter Par) and the distal arterial pressure (hereinafter Pd). These characteristic variables of the cardiac operational state will be grouped together hereinafter in a vector xc. Other variables of interest relate to certain modeling parameters that are liable to change over time as a function of the state of the patient, and these parameters comprise in particular the contractility (hereinafter s0), the active stiffness (hereinafter k0) and the peripheral resistance (hereinafter Rd). These parameters are grouped together in a vector denoted T. Lastly, diverse indicators may be derived from the vector xc and from the modeling parameters T so as to allow the change in the condition to be monitored. These indicators, comprising in particular the cardiac output (hereinafter Q), will be denoted hereinafter by a vector CI.

The vector xc and the vector T are linked by equations (10) to (60) of Appendix A, in which equations (10), (20), (30), (40), (50) and (60) denote independent relations, and equations (11) to (18) define members of equation (10). The article by M. Camel et al, 'Dimensional reductions of a cardiac model for effective validation and calibration', Biomech Model Mechanobiol, 2013, describes these equations in detail.

The system formed by equations (10) to (60) may be summarized in the form of equation (100).

Once this cardiac model has been defined, a mechanical cardio-thoracic force model may be used. This model is a transfer function that converts the vector xc into a force exerted on the thorax by the heart.

This model is summarized in the form of equation (110), in which f(t) represents the force exerted by the heart in the state associated with the vector xc(t), kcon represents a stiffness and ycon a distance at rest between the thorax and the heart.

On the basis of this force, a thoracic model may be applied in order to determine the movements of the thorax under the effect of the force exerted by the heart. Generally, the thorax may be modeled as a set of eigenmodes, that is to say movement functions that are independent of one another and depend on the application of a modal force component.

The thoracic model may be summarized in the form of equation (120), in which the matrix At represents the dynamics of the system of eigenmodes modeling the thorax, and xt represents the vector describing the state of the thorax in this model. Equation (125) shows an exemplary implementation of this model, in which the vector xt is modeled by at and its time derivative, where at is the component of each mode used for the model, w is the angular frequency specific to each mode used for the model, xsi is the damping coefficient of each mode used for the model, and b is the modal excitation coefficient of each mode used for the model.

Lastly, on the basis of the vector xt describing the thorax, it is possible to determine an equivalent acceleration z(t) of the thorax by way of equation (130), in which the function h( ) is a transfer function applied to the vector xt of the state of the thorax.

In an ideal situation, it would therefore be possible to measure the acceleration z(t) of the thorax so as to trace back to the vector xc and to the vector T via equations (100) to (130), allowing the change in the relevant parameters to be monitored.

However, the device 2 is not able to measure the acceleration of the thorax perfectly, even after noise removal. All of the data that may be derived are therefore approximations.

To mitigate this problem, and also the fact that the operators Ac and At along with the functions f( ) and h( ) are not necessarily reversible, the Applicant has arranged a function Calc( ) that supplements the model described above, and has discretized these functions and operators.

Thus, the Applicant has introduced, with equation (140), an innovative vector that measures the difference between the measurement with noise removed Z(t) and the theoretical measurement z(t). The innovative vector is then reintroduced into correction functions based on a Kalman filter, or on a combination of a Kalman filter and a Luenberger observer, as disclosed in the article by Moireau et al. 'Joint state and parameter estimation for distributed mechanical systems', Comput. Methods Appl. Mech. Engrg. 197 (2008) 659-677. These correction functions have the advantage of ensuring convergence in a wide range of situations, in a few operating loops.

As a result, the Applicant has introduced equations (200) and (220) so as to modify equations (100) and (120) in order to take these corrections into account, and introduced equation (205) so as to take their effects on the vector T into account.

The computer 8 may also receive signals measured by other sensors, in particular non-invasive measurements of variables linked to hemodynamics (tensiometer, radial tonometry, photoplethysmogram, etc.), and combine them with the cardiac data determined by the computer 8 in order to derive therefrom cardiac indicators allowing monitoring of specific cardiac conditions.

Figure 2:
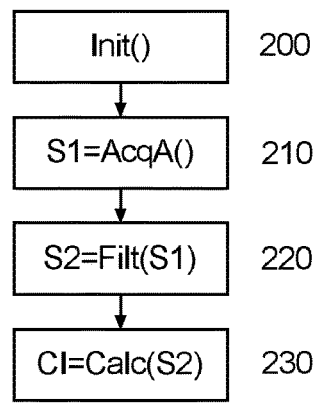
FIG. 2 shows an exemplary implementation of a function executed by the device of FIG. 1.

FIG. 2 shows an example of a function implemented by the device 2. In an operation 200, the device 2 executes a function Init( ). The function Init( ) initializes the device 2, in particular by selecting parameters specific to the patient that relate to the cardiovascular model and/or to the thoracic model. This function may perform a calibration operation each time the device 2 is turned on, or perform this calibration periodically or once and for all.

Next, in an operation 210, the accelerometer 4 measures the vibrations of the thorax of the patient and derives the signal S1 therefrom, and then, in an operation 220, the filter 6 executes a function Filt( ) so as to process the signal S1 and obtain the signal S2. For example, the function Filt( ) may implement the filtering described in the thesis by A. Laurin 'New timing estimations of cardiovascular events; application to seismocardiography, microneurography, and blood pressure'.

Lastly, in an operation 230, the computer 8 executes a function Calc( ) that applies the thoraco-cardiovascular model to the signal S2 in order to derive the cardiac data CI therefrom.

Figure 3:
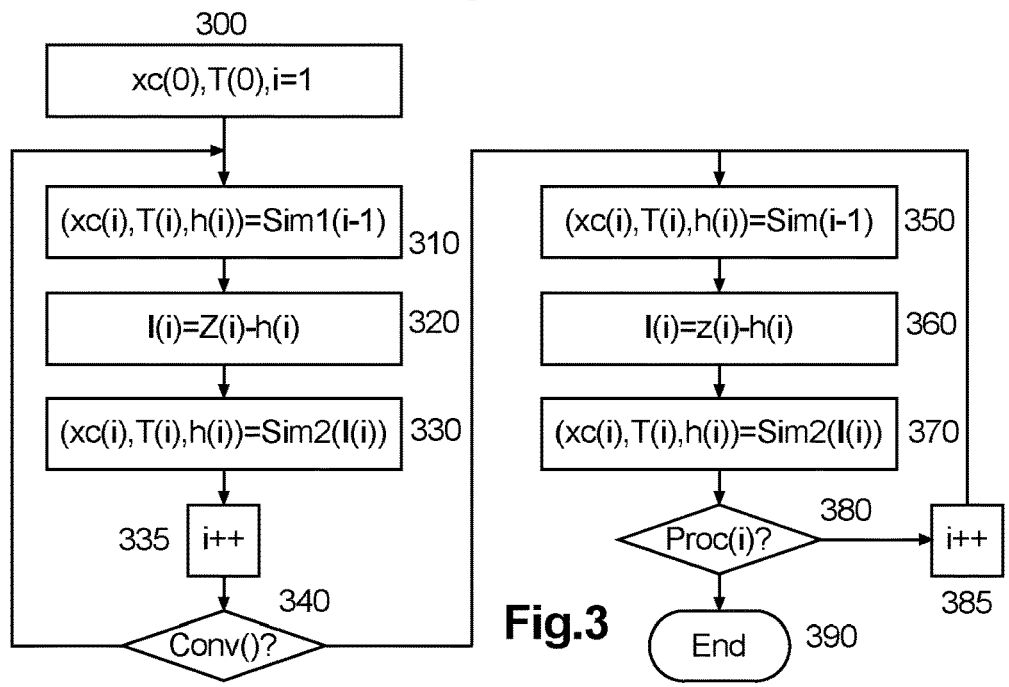
FIG. 3 shows an exemplary implementation of an operation of FIG. 2, and FIGS. 4 to 6 show examples of signals acquired by the device of FIG. 1, before filtering, after filtering and after a shaping processing operation, respectively.

FIG. 3 shows an exemplary implementation of the function Calc( ).

The function Calc( ) comprises two loops with identical operation, the first of which is used for initialization and the second of which is used for operation.

In an operation 300, the function Calc( ) starts with initialization values of the vectors xc and T, and with a time index i.

Next, in an operation 310, a function Sim1( ) is applied with the index i−1 as argument. The function Sim1( ) sequentially applies a discretized version of equations (100) to (130), in order to determine what the value of z(t) would be for the instant corresponding to the instant i, as computed using the theoretical model.

Equations (300) to (330) represent one possible discretized version, discretized by what is called an explicit method, of equations (100) to (130) applied by the function Sim(1).

Next, in an operation 320, the computer 8 computes the innovative vector by applying equation (140), and the simulation is repeated in an operation 330 with a function Sim2( ).

The function Sim2( ) receives the innovative vector I(i) so as to apply equations (200) to (220), in a form discretized in the same way as equations (300) to (330), as may be seen with equations (400) to (430). In practice, the function Sim2( ) applies a correction derived from the innovative vector to the computations already performed using the function Sim1( ). As a variant, the function Sim2( ) could completely restart the computations.

Next, in an operation 335, the index i is incremented and a function Cony( ) is executed in an operation 340 in order to compare the difference between the value h(i) resulting from operation 330 and the measurement Z(i) coming from the accelerometer 4 used in operation 320.

When this difference is greater than a chosen threshold, then it is considered that the correction functions are not yet sufficient, and the function Calc( ) restarts with operation 310.

As mentioned above, the convergence by the correction functions is achieved quite quickly, for example from measurements of the accelerometer that are associated with a single heartbeat.

When the difference is less than the chosen threshold, then it is considered that the determined values are useful, and the second loop starts.

In the second loop, operations 350 to 370, identical to operations 310 to 330, are executed in order to determine the current values of the vector xt(i) and T(i). Next, in an operation 380, these measurements are displayed and/or subjected to a processing operation relating to the monitoring of the condition with the execution of a function Proc( ). The function Proc( ) also determines whether there are still data to be processed. If this is the case, then the index i is incremented in an operation 385, and the second loop restarts with operation 350. Otherwise, the function Calc( ) ends in an operation 390.

On the basis of the computations of the function Calc( ), a set of functions may be implemented, comprising transmitting a warning signal to the user or to a member of medical staff (locally or by remote communication), displaying the computed vectors xc and T, computing cardiac indicators CI from the vectors xc and T, etc.

The device of the invention makes it possible to supplement or even to replace a plurality of measuring apparatuses that were used previously but not necessarily synchronized with one another. In addition, it makes it possible to produce measurements that are able to be interpreted directly in situations where medical staff previously had to interpret graphs.

The computing function may implement thoraco-cardiovascular models other than the one given here by way of example, and receive and pre-process signals measured by other sensors, in particular non-invasive measurements of variables linked to hemodynamics (tensiometer, radial tonometry, photoplethysmogram, etc.).

APPENDIX A $$\rho d_0 \ddot{y} + \frac{d_0}{R_0}\left(1 + \frac{y}{R_0}\right)\Sigma_{sph} = P_v\left(1 + \frac{y}{R_0}\right)^2 \quad (10)$$

$$\Sigma_{sph} = \sigma_{1D} + 4(1 - C^{-3})\left(\frac{\partial W_e}{\partial J_1} + C\frac{\partial W_e}{\partial J_2}\right) + 2\frac{\partial W_e}{\partial J_4} + 2\eta\dot{C}(1 - 2C^{-6}) \quad (11)$$

$$\sigma_{1D} = E_S \frac{e_{1D}}{(1 + 2e_c)^2} \quad (12)$$

$$C = \left(1 + \frac{y}{R_0}\right)^2 \quad (13)$$

$$e_{1D} = \frac{C - 1}{2} \quad (14)$$

$$f_{va}(P_v, P_{ar}, P_{ar}) = -4\pi R_0^2\left(1 + \frac{y}{R_0}\right)^2 \dot{y} \quad (15)$$

$$J_1 = 2C + C^{-2} \quad (16)$$

$$J_4 = C \quad (17)$$

$$W_e(J_1, J_4) = k_1 e^{k_2(J_1 - 3)^2} + k_3 e^{k_4(J_4 - 1)^2} \quad (18)$$

$$(t_c + \mu\dot{e}_c) = E_S \frac{(e_{1D} - e_c)(1 + 2e_{1D})}{(1 + 2e_c)^3} \quad (20)$$

$$\dot{k}_c = -(|\bar{u}| + \alpha|\dot{e}_c|)k_c + n_0 k_0 |\bar{u}| \quad (30)$$

$$\dot{t}_c = -(|\bar{u}| + \alpha|\dot{e}_c|)t_c + n_0 s_0 |\bar{u}| + k_c \dot{e}_c \quad (40)$$

$$C_p \dot{P}_{ar} + \frac{(P_{ar} - P_d)}{R_p} = 4\pi R_0^2 \left(1 + \frac{y}{R_0}\right)^2 \dot{y} \quad (50)$$

$$C_p \dot{P}_d + \frac{(P_d - P_{ar})}{R_p} = \frac{(P_{sv} - P_d)}{R_p} \quad (60)$$

$$\dot{x}_c = A_c(x_c, T, t) \quad (100)$$

$$f(t) = k_{con}\max(y(t) - y_{con}; 0) \quad (110)$$

$$\dot{x}_t = A_t(x_t, t) + f(t) \quad (120)$$

$$\begin{bmatrix} \dot{a}t \\ \ddot{a}t \end{bmatrix} = \begin{bmatrix} 0 & 1 \\ -w^2 & -2xsi\,w \end{bmatrix}\begin{bmatrix} at \\ \dot{a}t \end{bmatrix} + \begin{bmatrix} 0 \\ bf(t) \end{bmatrix} \quad (125)$$

$$z(t) = h(\dot{x}_t) \quad (130)$$

$$I(t) = Z(t) - h(\dot{x}_t) \quad (140)$$

$$\dot{x}_c = A_c(x_c, T, t) + K_c(I(t), t) \quad (200)$$

$$\dot{T} = K_T(I(t), t) \quad (205)$$

$$\dot{x}_t = A_t(x_t, t) + f(t) + K_t(I(t), t) \quad (220)$$

$$x_c(t_{i+1}) = A_c(x_x(t_i), T(t_i), t_i)(t_{i+1} - t_i) + x_c(t_i) \quad (300)$$

$$f(t_{i+1}) = k_{con}\max(y(t_{i+1}) - y_{con}; 0) \quad (310)$$

$$x_t(i+1) = (A_t(x_t(t_i), t_i) + f(t_i))(t_{i+1} - t_i) + x_t(t_i) \quad (320)$$

$$z(t_{i+1}) = h\left(\frac{x_t(t_{i+1}) - x_t(t_i)}{(t_{i+1} - t_i)}\right) \quad (330)$$

$$x_c(t_{i+1}) = (A_c(x_c(t_i), T(t_i), t_i) + K_c(I(t_{i+1}), t_{i+1}))(t_{i+1} - t_i) + x_c(t_i) \quad (400)$$

$$T(t_{i+1}) = K_T(I(t_{i+1}), t_{i+1})(t_{i+1} - t_i) + T(t_i) \quad (405)$$

$$f(t_{i+1}) = k_{con}\max(y(t_{i+1}) - y_{con}; 0) \quad (410)$$

$$x_t(i+1) = (A_t(x_t(t_i), t_i) + f(t_i) + K_t(I(t_{i+1}), t_{i+1}))(t_{i+1} - t_i) + x_t(t_i) \quad (420)$$

$$z(t_{i+1}) = h\left(\frac{x_t(t_{i+1}) - x_t(t_i)}{(t_{i+1} - t_i)}\right) \quad (430)$$

The invention claimed is:

1. A cardiac device comprising an accelerometer and a filter arranged to remove noise from an SCG signal derived from the accelerometer, characterized in that the cardiac device furthermore comprises a computer arranged to apply a thoraco-cardiovascular model to the signal coming from the filter and to derive at least one cardiac activity indicator (CI) therefrom, the thoraco-cardiovascular model comprising:
    a cardiovascular model, the cardiovascular model including parameters for modeling a heart, variables representing a state of the heart, and a law representing contact forces applied to a thoracic cavity by the heart; and
    a thoracic model, the thoracic model including a transfer function between the contact forces applied by the heart and an acceleration induced in the thoracic cavity.

2. The device as claimed in claim 1, wherein the computer is arranged to compute the cardiac activity indicator (CI) by applying the thoraco-cardiovascular model in order to compute a theoretical SCG signal value, and by applying at least one correction function based on the difference between the theoretical SCG signal value and a corresponding value based on the signal coming from the filter.

3. The device as claimed in claim 2, wherein the computer is arranged to apply at least one Kalman filter or a combination of a Kalman filter and a Luenberger observer in said at least one correction function.

4. The device as claimed in claim 1, wherein the thoracic model comprises a cardiothoracic force transfer function and a thoracic mechanical model.

5. The device as claimed in claim 1, wherein the accelerometer and the computer are accommodated in a single housing of the device.

6. The device as claimed in claim 1, wherein the accelerometer and the computer are accommodated in two separate housings of the device.

7. The device as claimed in claim 1, furthermore arranged to transmit a signal as a function of a comparison between a computed cardiac activity indicator and a threshold value.

8. The device as claimed in claim 1, wherein the computer is arranged to receive and process variables linked to hemodynamics.

9. A cardiac monitoring method, comprising:
    obtaining an SCG signal from an accelerometer,
    filtering the SCG signal,
    applying a thoraco-cardiovascular model to the filtered SCG signal and taking at least one cardiac activity indicator therefrom, the thoraco-cardiovascular model comprising:
        a cardiovascular model, the cardiovascular model including parameters for modeling a heart, variables representing a state of the heart, and a law representing contact forces applied to a thoracic cavity by the heart; and
        a thoracic model, the thoracic model including a transfer function between the contact forces applied by the heart and an acceleration induced in the thoracic cavity.

10. The method as claimed in claim 9, wherein the application of the thoraco-cardiovascular model comprises:

applying the thoraco-cardiovascular model in order to compute a theoretical SCG signal value, determining a difference between the theoretical SCG signal value and a corresponding value based on the filtered SCG signal, applying at least one correction function based on the difference in order to determine the cardiac activity indicator.

* * * * *